United States Patent [19]

Chang et al.

[11] Patent Number: 5,780,703

[45] Date of Patent: Jul. 14, 1998

[54] PROCESS FOR PRODUCING LOW AROMATIC DIESEL FUEL WITH HIGH CETANE INDEX

[75] Inventors: Clarence D. Chang, Princeton, N.J.; Stuart D. Hellring, Yardley, Pa.; David O. Marler, Deptford, N.J.; Jose G. Santiesteban, Yardley; James C. Vartuli, West Chester, both of Pa.

[73] Assignee: Mobil Oil Corporation, Fairfax, Va.

[21] Appl. No.: 513,107

[22] Filed: Aug. 9, 1995

Related U.S. Application Data

[63] Continuation-in-part of Ser. No. 236,073, May 2, 1994, Pat. No. 5,510,309.

[51] Int. Cl.$^6$ .............................. C07C 2/58; C10G 35/04
[52] U.S. Cl. .................. 585/732; 585/709; 585/721; 208/141; 208/144
[58] Field of Search ....................... 585/709, 722, 585/266, 732; 208/141, 144; 581/721

[56] References Cited

U.S. PATENT DOCUMENTS

| | | | |
|---|---|---|---|
| Re. 28,398 | 4/1975 | Chen et al. | 208/111 |
| 3,668,113 | 6/1972 | Burbidge et al. | 208/97 |
| 3,755,138 | 8/1973 | Chen et al. | 208/33 |
| 3,917,564 | 11/1975 | Meyers | 208/31 |
| 3,956,102 | 5/1976 | Chen et al. | 208/93 |
| 3,960,978 | 6/1976 | Givens et al. | 260/683.15 |
| 4,021,502 | 5/1977 | Plank et al. | 260/683.15 |
| 4,100,056 | 7/1978 | Reynolds | 208/57 |
| 4,100,218 | 7/1978 | Chen et al. | 260/673 |
| 4,150,062 | 4/1979 | Garwood et al. | 260/673 |
| 4,211,640 | 7/1980 | Garwood et al. | 208/255 |
| 4,227,992 | 10/1980 | Garwood et al. | 208/46 |
| 4,400,265 | 8/1983 | Shen | 208/97 |
| 4,422,155 | 12/1983 | Cook | 2/8 |
| 4,447,312 | 5/1984 | Angevine et al. | 208/46 |
| 4,456,781 | 6/1984 | Marsh et al. | 585/533 |
| 4,483,760 | 11/1984 | Tabak et al. | 208/60 |
| 4,874,505 | 10/1989 | Bartilucci et al. | 208/131 |
| 4,922,048 | 5/1990 | Harandi | 585/310 |
| 4,922,051 | 5/1990 | Nemet-Mavrodin et al. | 585/418 |
| 4,990,239 | 2/1991 | Derr, Jr. et al. | 208/68 |
| 5,098,684 | 3/1992 | Kresge et al. | 423/277 |
| 5,102,643 | 4/1992 | Kresge et al. | 423/328 |
| 5,113,034 | 5/1992 | Soled et al. | 585/510 |
| 5,227,552 | 7/1993 | Chang et al. | 585/257 |
| 5,345,026 | 9/1994 | Chang et al. | 585/700 |
| 5,382,731 | 1/1995 | Chang et al. | 585/315 |
| 5,401,478 | 3/1995 | Chang et al. | 423/235 |
| 5,449,847 | 9/1995 | Chang et al. | 585/266 |
| 5,453,556 | 9/1995 | Chang et al. | 585/524 |
| 5,510,309 | 4/1996 | Chang et al. | 502/308 |

FOREIGN PATENT DOCUMENTS

| | | |
|---|---|---|
| 0 585 065 | 3/1994 | European Pat. Off. |
| WO 94/14732 | 7/1994 | European Pat. Off. |
| 1-288339 | of 1989 | Japan |

OTHER PUBLICATIONS

Hino, M. et al., "Synthesis of Solid Superacid of Tungsten Oxide Supported Zirconia and Its Catalytic Action of Reactions of Butane and Pentane," J. Chem. Soc., Chem. Commun., 1259–1260 (1988).

Arata, K. and Hino, M., Proceedings 9th Intern. Congress on Catalysis, vol. 4, "Oxide Catalysts and Catalyst Development," M. J. Phillips et al., ed., 1727–1735 (1988).

Iglesia, E., Soled, S.L., and Kramer, G.M., Isomerization of Alkanes on Sulfated Zirconia: Promotion by Pt and by Adamantyl Hydride Transfer Species, Journal of Catalysis 144, 238–253 (1993).

Hsu, C.-Y., Heimbuch, C.R. Armes, C.T., and Gates, B.C., "A Highly Active Solid Superacid Catalyst for n–Butane Isomerization: A Sulfated Oxide Containing Iron, Manganese and Zirconium," J. Chem. Soc., Chem. Commun., 1645 (1992).

The Oil and Gas Journal, Jan. 6, 1975, pp. 69–73.

Hydrocarbon Processing, vol. 61, No. 5, May 1982 pp. 110–112.

Hydrocarbon Processing, vol. 60, No. 9, Sep. 1981, pp. 134–138.

Albright, L.F. et al., "Alkylation of Isobutane with $C_4$ Olefins," Ind. Eng. Chem. Res., 381–386 1988.

The Handbook of Petroleum Refining Processes, 23–28 R.A. Meyers, Ed., 1986.

Primary Examiner—Bekir Yildirim
Attorney, Agent, or Firm—Thomas W. Steinberg; Malcolm D. Keen

[57] ABSTRACT

A process for converting at least one olefin and at least one isoparaffin to a diesel fuel blending component comprising the steps of contacting the olefin and the isoparaffin with a catalyst comprising an acidic solid comprising a Group IVB metal oxide modified with an oxyanion of a Group VIB metal to provide a diesel fuel. Process conditions can be varied to favor the formation of gasoline, distillate, lube range products or mixtures thereof.

16 Claims, No Drawings

PROCESS FOR PRODUCING LOW AROMATIC DIESEL FUEL WITH HIGH CETANE INDEX

This application is a continuation-in-part of U.S. Ser. No. 08/236,073, filed May 2, 1994, now U.S. Pat. No. 5,510,309, issued Apr. 23, 1996, the entire contents of which are hereby incorporated by reference.

FIELD OF THE INVENTION

The present invention relates to a process for producing low aromatic diesel fuel with a high cetane index. Particularly, the invention relates to a process for selectively upgrading lower boiling range feedstocks into higher boiling range fuels having a desired composition.

BACKGROUND OF THE INVENTION

Recent regulatory developments have led refiners to seek methods for reformulating motor fuels, including gasoline and diesel fuel, to meet increasingly stringent air quality requirements. These techniques include reducing the olefin and aromatic content of the motor fuels while maintaining the desired operational characteristics as predicted by the octane or cetane rating of the fuel.

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate.

Industrial alkylation processes have historically used large volumes of liquid Bronsted acid catalysts such as hydrofluoric or sulfuric acid under relatively low temperature conditions. Acid strength is preferably maintained at 88 to 94 weight percent by the continuous addition of fresh acid and the continuous withdrawal of spent acid. Liquid acid catalyzed isoparaffin:olefin alkylation processes share inherent drawbacks including environmental and safety concerns, acid consumption, and sludge disposal. For a general discussion of sulfuric acid alkylation, see the series of three articles by L.F. Albright et al., "Alkylation of Isobutane with $C_4$ Olefins", 27 *Ind. Eng. Chem. Res.*, 381–397, (1988). For a survey of hydrofluoric acid catalyzed alkylation, see 1 *Handbook of Petroleum Refining Processes* 23–28 (R. A. Meyers, ed., 1986).

The typical petroleum refinery generates numerous olefinic streams, which, upon hydrogenation and optional fractionation, would be useful gasoline blending components. Examples of such streams include the olefinic gasoline and naphtha by-products of catalytic hydrodewaxing processes such as the MLDW (Mobil Lubricant Dewaxing) and MDDW (Mobil Distillate Dewaxing). Additional examples include olefinic gasoline cuts from delayed coking units (thermally cracked gasoline), as well as from catalytic cracking process units such as a Fluidized Catalytic Cracking (FCC) process. Lighter olefins may be easily dimerized or oligomerized to provide suitable feedstocks, for example in a process such as MOGD/MOGDL (Mobil Olefins to Gasoline and Distillate/Mobil Olefins to Gasoline, Distillate and Lube Stock), or MOCI (Mobil Olefins to Chemical Intermediates). Examples of processes which produce olefinic stocks include the processes taught in U.S. Pat. Nos. 4,922,048 to Harandi and 4,922,051 to Nemet-Mavrodin et al. Additional examples of light olefin dimerization/oligomerization processes include Dimersol (light olefin dimerization), Isopol (selective isobutene isomerization) and Selectopol (selective butadiene polymerization). See *Hydrocarbon Processing*, Vol. 61, No. 5, May 1982, pp. 110–112, and *Hydrocarbon Processing*, Vol. 60, No. 9, September 1981, pp. 134–138.

Recent regulatory changes have created an incentive for refiners to reduce the olefins and aromatics content of motor fuels. The final version of the complex model issued by the United States Environmental Protection Agency (US EPA) to predict the consequence of various fuel components on combustion emissions creates a significant penalty for high RVP components in gasoline. At the same time, both the US EPA and state regulatory boards such as the California Air Resources Board (CARB) have instituted regulations on diesel fuel which set an upper limit on aromatics and sulfur contents, and a lower limit for cetane index. In general, sulfur must remain below 500 ppm. U.S. EPA requires either less than 35 wt % aromatics or a minimum of 40 cetane index. CARB limits aromatics to 10 wt % unless a waiver fuel is approved. Both regulatory agencies require a maximum $T_{90}$ of 640° F. By alkylating light olefins, such as $C_3$–$C_5$ olefins, with light isoparaffins, such as isobutane and isopentane, high RVP gasoline components are converted into diesel range fuel which meets most of the regulatory restrictions.

SUMMARY OF THE INVENTION

A mixed stream of isoparaffin, such as isobutane or isopentane, and olefins, such as propylene, butenes, pentenes, or hexenes, are passed over a catalyst which comprises an acidic solid comprising a Group IVB metal oxide modified with an oxyanion of a Group VIB metal in a fixed-bed under pressure at sufficiently high temperature to produce diesel range fuel. Process conditions can be varied to favor the formation of either gasoline, distillate, lube range products or mixtures thereof. The feed olefins can come from among many sources including FCC olefins, MTBE raffinate, TAME raffinate, etc. A detailed description of possible olefins sources is outlined in U.S. Pat. No. 5,227,552, to Chang, Hellring and Striebel, which is incorporated by reference as if set forth at length herein. The isoparaffin can come from FCC, hydrocracking, etc. process or by isolation of field production off-gases. Generally, $C_4$–$C_8$ isoparaffins and preferably $C_4$–$C_5$ isoparaffins are used in the present invention.

DETAILED DESCRIPTION

Olefinic feedstocks suitable for use in the present invention include numerous olefinic streams produced by petroleum refining operations, for example, a cracked olefinic stream such as an olefinic gasoline boiling range fraction from a delayed coker process unit. The olefinic feedstocks generally comprises $C_2$–$C_{10}$ olefins and preferably $C_3$–$C_8$ olefins. Delayed coking processes are taught in U.S. Pat. No. 3,917,564 to Meyers and U.S. Pat. No. 4,874,505 to Bartilucci et al., both of which patents are incorporated herein by reference.

Suitable olefinic feedstocks are also produced as byproducts in catalytic dewaxing processes, as described in U.S. Pat. No. 4,922,048, which patent is incorporated herein by reference.

Catalytic dewaxing of hydrocarbon oils to reduce the temperature at which precipitation of waxy hydrocarbons occurs is a known process and is described, for example, in the Oil and Gas Journal, Jan. 6, 1975, pages 69–73. A number of patents have also described catalytic dewaxing processes. For example, U.S. Pat. RE. No. 28,398 describes a process for catalytic dewaxing with a catalyst comprising a medium-pore zeolite and a hydrogenation/dehydrogenation component. U.S. Pat. No. 3,956,102 describes a process for hydrodewaxing a gas oil with a medium-pore zeolite catalyst. U.S. Pat.No. 4,100,056 describes a Mordenite catalyst containing a Group VI or a Group VIII metal which may be used to dewax a distillate derived from a waxy crude. U.S. Pat. No. 3,755,138 describes a process for mild solvent dewaxing to remove high quality wax from a lube stock, which is then catalytically dewaxed to specification pour point. Such developments in catalytic dewaxing have led to the MLDW (Mobil Lube Dewaxing) and MDDW (Mobil Distillate Dewaxing) process.

Catalytic dewaxing processes may be followed by other processing steps such as hydrodesulfurization and denitrogenation in order to improve the qualities of the product. For example, U.S. Pat. No. 3,668,113 describes a catalytic dewaxing process employing a Mordenite dewaxing catalyst which is followed by a catalytic hydrodesulfurization step over an alumina-based catalyst. U.S. Pat. No. 4,400,265 describes a catalytic dewaxing/hydrodewaxing process using a zeolite catalyst having the structure of ZSM-5 wherein gas oil is catalytically dewaxed followed by hydrodesulfurization in a cascade system. The foregoing dewaxing processes exemplify low-severity medium-pore catalyzed dewaxing processes which produce a low octane naphtha by-product. Another example of a low severity medium-pore catalyzed conversion reaction is olefin oligomerization.

Recent developments in zeolite catalysts and hydrocarbon conversion methods and apparatuses have created interest in utilizing olefinic feedstocks for producing heavier hydrocarbons, such as $C_5+$ gasoline, distillate or lubes. These developments form the basis of the Mobil olefins to gasoline/distillate (MOGD) method and apparatus, and the Mobil olefins to gasoline/distillate/lubes (MOGDL) method and apparatus.

In MOGD and MOGDL, olefins are catalytically converted to heavier hydrocarbons by catalytic oligomerization using an acid crystalline zeolite, such as a zeolite catalyst having the structure of ZSM-5. Process conditions can be varied to favor the formation of either gasoline, distillate or lube range products. U.S. Pat. Nos. 3,960,978 and 4,021,502 to Plank et al. disclose the conversion of $C_2$–$C_5$ olefins alone or in combination with paraffinic components, into higher hydrocarbons over a crystalline zeolite catalyst. U.S. Pat. Nos. 4,150,062; 4,211,640 and 4,227,992 to Garwood et al. have contributed improved processing techniques to the MOGD system. U.S. Pat. No. 4,456,781 to Marsh et al. has also disclosed improved processing techniques for the MOGD system.

U.S. Pat. Nos. 4,422,185 and 4,483,760 to Tabak disclose two-stage catalytic processes for upgrading hydrocarbon feedstocks, the texts of which are incorporated by reference as if set forth at length herein.

The '185 patent to Tabak teaches a process for converting an olefinic feedstock containing ethene and heavier alkenes to a product rich in distillate and olefinic gasoline. Effluent from a first stage distillate mode reactor is flashed to separate an ethylene-rich product stream which is then charged to a second stage gasoline mode reactor. A disadvantage of the process taught by '185 is that the highly olefinic gasoline product stream is of a relatively low octane and reduces the gasoline pool octane.

The '760 patent to Tabak teaches a process for catalytically dewaxing a middle distillate separating an olefinic by-product from the dewaxed distillate product stream, and upgrading a gasoline fraction at temperatures above 900° F. In addition, the second catalytic reactor is operated to convert at least 10 wt. % of the olefinic by-product fraction to fuel oil (material boiling above 3800° F.).

Olefinic feedstocks may be obtained from various sources, including from fossil fuel processing streams such as gas separation units, from the cracking of $C_2$-hydrocarbons, such as LPG (liquified petroleum gas) from coal by-products, from various synthetic fuel processing streams, and as by-products from fluid catalytic cracking (FCC) and thermal catalytic cracking (TCC) process units. U.S. Pat. No. 4,100,218 to Chen et al. teaches thermal cracking of ethane to ethylene, with subsequent conversion of ethylene to LPG and gasoline over a zeolite catalyst having the structure of ZSM-5.

Distillate products produced over a broad range of conversion conditions useful in the present process have a cetane index of at least about 35 and preferably have at least about a 45 cetane index.

Conversion is inversely proportional with $WHSV_{olein\ on\ catalyst}$ for a given temperature. Between 0.1 and 1.0 WHSV, reactor temperature must be above about 350° F. in order to achieve $C_5$-olefin conversions above 90%. If temperature is restricted to 375° F. to limit aromatics to 10 wt %, $WHSV_{olefin\ on\ catalyst}$ must be held below about 0.3 to maintain 90% or greater pentenes conversion.

The term "yield" as used herein is defined as the weight of product per weight of converted olefin. Total product yields above unity indicate that isoparaffin has been incorporated into the products. Maximum gasoline yield in isobutane/butene alkylation results from combination of one mole of each reactant to provide a yield slightly above 2.0. Ideally, a diesel range fuel is produced by reacting more than one mole of olefin per isoparaffin. For instance, a mole of isobutane must combine with two or three moles of butene to reach sufficient molecular weight to enter the boiling range of diesel fuel. Likewise, a mole of isopentane would require two moles of pentene to reach diesel range and would give a yield of about 1.5. Therefore, diesel production in the present invention uses a lower isoparaffin/olefin molar ratio than typically is used for producing gasoline from a similar reactor feed stream.

| | Process Conditions | |
|---|---|---|
| | Broad Range | Preferred Range |
| Temperature | 100–500° F. | 200–400° F |
| Pressure | 0–1500 psig | 50–1000 psig |
| Olefin WHSV (Zeolite Basis) | 0.01–10 | 0.1–5.0 |
| Isoparaffin:Olefin Molar Ratio in Feedstock | 0.1–100 | 0.25–50 |

The product slates can be adjusted by varying the operating conditions. In general higher cetane index of the diesel range product is favored by higher olefin WHSV and lower temperatures in the above ranges. Gasoline yields are maximized at higher temperatures and higher isoparaffin:olefin molar ratios in the above ranges. Distillate production is favored by higher isoparaffin:olefin molar ratios and lower temperatures in the above ranges.

The reaction temperature can be limited to obtain a range of aromatics content in the diesel fuel product. In cases where isopentane is reacted with pentenes, lower temperatures in the above ranges result in low wt. % aromatics in the gasoline and distillate product. To produce a diesel range blending stock containing less than about 10 wt % aromatics, the reactor temperature is preferably kept below about 375° F. To meet the 35 wt % aromatics limit set by the US EPA, reactor temperature is preferably controlled below about 440° F.

In cases where an increased amount of the distillate fraction is desired the product boiling at a cut point up to about 450° F. may be recycled to the contacting step. The product boiling at a cut point up to about 390° F. may also be recycled to the contacting step.

Optionally, the product of the present invention can be further hydrotreated by conventional methods to reduce product olefins by saturation.

The acidic solid material useful as a catalyst in the present process may be prepared in accordance with U.S. patent application Ser. Nos. 08/332,169, filed Oct. 31, 1994; 08/236,073, filed May 2, 1994; 08/143,716, filed Nov. 1, 1993; and 08/136,838, filed Oct. 18, 1993, the entire disclosures incorporated herein by reference.

The solid material described herein comprises an oxide of a Group IVB metal, preferably zirconia or titania. This Group IVB metal oxide is modified with an oxyanion of a Group VIB metal, such as an oxyanion of tungsten, such as tungstate. The modification of the Group IVB metal oxide with the oxyanion of the Group VIB metal imparts acid functionality to the material. The modification of a Group IVB metal oxide, particularly, zirconia, with a Group VIB metal oxyanion, particularly tungstate, is described in U.S. Pat. No. 5,113,034; in Japanese Kokai Patent Application No. Hei 1 [1989]-288339; and in an article by K. Arata and M. Hino in *Proceedings 9th International Congress on Catalysis*, Volume 4, pages 1727–1735 (1988), the entire disclosures of these publications are expressly incorporated herein by reference. According to these publications, tungstate is impregnated onto a preformed solid zirconia material to yield a solid superacid catalyst with an acid strength of Ho less than or equal to −14.52.

For the purposes of the present disclosure, the expression, Group IVB metal oxide modified with an oxyanion of a Group VIB metal, is intended to connote a material comprising, by elemental analysis, a Group IVB metal, a Group VIB metal and oxygen, with more acidity than a simple mixture of separately formed Group IVB metal oxide mixed with a separately formed Group VIB metal oxide or oxyanion. The present Group IVB metal, e.g., zirconium, oxide modified with an oxyanion of a Group VIB metal, e.g., tungsten, is believed to result from an actual chemical interaction between a source of a Group IVB metal oxide and a source of a Group VIB metal oxide or oxyanion.

This chemical interaction is discussed in the aforementioned article by K. Arata and M. Hino in *Proceedings 9th International Congress on Catalysis*, Volume 4, pages 1727–1735 (1988). In this article, it is suggested that solid superacids are formed when sulfates are reacted with hydroxides or oxides of certain metals, e.g., Zr. These superacids are said to have the structure of a bidentate sulfate ion coordinated to the metal, e.g., Zr. In this article, it is further suggested that a superacid can also be formed when tungstates are reacted with hydroxides or oxides of Zr. The resulting tungstate modified zirconia materials are theorized to have an analogous structure to the aforementioned superacids comprising sulfate and zirconium, wherein tungsten atoms replace sulfur atoms in the bidentate structure. It is further suggested that tungsten oxide combines with zirconium oxide compounds to create superacid sites at the time the tetragonal phase is formed.

Although it is believed that the present catalysts may comprise the bidentate structure suggested in the aforementioned article by Arata and Hino, the particular structure of the catalytically active site in the present Group IVB metal oxide modified with an oxyanion of a Group VIB metal has not yet been confirmed, and it is not intended that this catalyst component should be limited to any particular structure.

Suitable sources of the Group IVB metal oxide, used for preparing the catalyst, include compounds capable of generating such oxides, such as oxychlorides, chlorides, nitrates, oxynitrates, etc., particularly of zirconium or titanium. Alkoxides of such metals may also be used as precursors or sources of the Group IVB metal oxide. Examples of such alkoxides include zirconium n-propoxide and titanium i-propoxide. These sources of a Group IVB metal oxide, particularly zirconia, may form zirconium hydroxide, i.e., $Zr(OH)_4$, or hydrated zirconia as intermediate species upon precipitation from an aqueous medium in the absence of a reactive source of tungstate. The expression, hydrated zirconia, is intended to connote materials comprising zirconium atoms covalently linked to other zirconium atoms via bridging oxygen atoms, i.e., Zr—O—Zr, further comprising available surface hydroxy groups. When hydrated zirconia is impregnated with a suitable source of tungstate under sufficient conditions, these available surface hydroxyl groups are believed to react with the source of tungstate to form an acidic catalyst. As suggested in the aforementioned article by K. Arata and M. Hino in *Proceedings 9th International Congress on Catalysis*, Volume 4, pages 1727–1735 (1988), precalcination of $Zr(OH)_4$ at a temperature of from about 100° C. to about 400° C. results in a species which interacts more favorably with tungstate upon impregnation therewith. This precalcination is believed to result in the condensation of ZrOH groups to form a polymeric zirconia species with surface hydroxyl groups. This polymeric species is referred to herein as a form of a hydrated zirconia.

Suitable sources for the oxyanion of the Group VIB metal, preferably molybdenum or tungsten, include, but are not limited to, ammonium metatungstate or metamolybdate, tungsten or molybdenum chloride, tungsten or molybdenum carbonyl, tungstic or molybdic acid and sodium tungstate or molybdate.

The present catalyst may be prepared, for example, by impregnating the hydroxide or oxide, particularly the hydrated oxide, of the Group IVB metal with an aqueous solution containing an anion of the Group VIB metal, preferably tungstate or molybdate, followed by drying.

The present modified oxide material may also be prepared by treatment of a hydrated Group IVB metal oxide, such as hydrated zirconia, under sufficient hydrothermal conditions prior to contact with a source of a Group VIB metal oxyanion, such as tungstate. More particularly, refluxing hydrated zirconia in an aqueous solution having a pH of 7 or greater was beneficial. Without wishing to be bound by any theory, it is theorized that the hydrothermally treated, hydrated zirconia is better because it has higher surface area. It is also theoretically possible that the hydrothermal treatment alters surface hydroxyl groups on the hydrated zirconia, possibly in a manner which promotes a more desirable interaction with the source of tungstate later used.

The hydrothermal conditions may include a temperature of at least 50° C., e.g., at least 80° C., e.g., at least 100° C. The hydrothermal treatment may take place in a sealed vessel at greater than atmospheric pressure. However, a preferred mode of treatment involves the use of an open vessel under reflux conditions. Agitation of hydrated Group IVB metal oxide in the liquid medium, e.g., by the action of refluxing liquid and/or stirring, promotes the effective interaction of the hydrated oxide with the liquid medium. The duration of the contact of the hydrated oxide with the liquid medium may be at least 1 hour, e.g., at least 8 hours. The liquid medium for this treatment may have a pH of 7 or greater, e.g., 9 or greater. Suitable liquid mediums include water, hydroxide solutions (including hydroxides of $NH_4^+$, $Na^+$, $K^+$, $Mg^{2+}$, and $Ca^{2+}$), carbonate and bicarbonate solutions (including carbonates and bicarbonates of $NH_4^+$, $Na^+$, $K^+$, $Mg^{2+}$, and $Ca^{2+}$), pyridine and its derivatives, and alkyl/hydroxyl amines.

The present modified oxide material may also be prepared by combining a first liquid solution comprising a source of a Group IVB metal oxide with a second liquid solution comprising a source of an oxyanion of a Group VIB metal. This combination of two solutions takes place under conditions sufficient to cause co-precipitation of the modified oxide material as a solid from the liquid medium. Alternatively, the source of the Group IVB metal oxide and the source of the oxyanion of the Group VIB metal may be combined in a single liquid solution. This solution may then be subjected to conditions sufficient to cause co-precipitation of the solid modified oxide material, such as by the addition of a precipitating reagent to the solution. Water is a preferred solvent for these solutions.

The temperature at which the liquid medium is maintained during the co-precipitation may be less than about 200° C., e.g., from about 0° C. to about 200° C. This liquid medium may be maintained at an ambient temperature (i.e., room temperature) or the liquid may be cooled or heated. A particular range of such temperatures is from about 30° C. to about 150° C.

The liquid medium from which the present catalyst components are co-precipitated may optionally comprise a solid support material, in which case the present catalyst may be co-precipitated directly onto the solid support material. Examples of such support materials include the material designated M41S, which is described in U.S. Pat. No. 5,102,643. A particular example of such an M41S material is a material designated MCM-41, which is described in U.S. Pat. No. 5,098,684.

Support materials and/or co-catalyst materials may also, optionally, be co-precipitated from the liquid medium along with the Group IVB metal oxide and the oxyanion of the Group VIB metal. An example of a co-catalyst material is a hydrogenation/dehydrogenation component.

According to an optional modification of the solid material described herein, a hydrogenation/dehydrogenation component is combined with the material. This hydrogenation/dehydrogenation component imparts the ability of the material to catalyze the addition of hydrogen to or the removal of hydrogen from organic compounds, such as hydrocarbons, optionally substituted with one or more heteroatoms, such as oxygen, nitrogen, metals or sulfur, when the organic compounds are contacted with the modified material under sufficient hydrogenation or dehydrogenation conditions.

Examples of hydrogenation/dehydrogenation components include the oxide, hydroxide or free metal (i.e., zero valent) forms of Group VIII metals (i.e., Pt, Pd, Ir, Rh, Os, Ru, Ni, Co and Fe), Group IVA metals (i.e., Sn and Pb), Group VB metals (i.e., Sb and Bi) and Group VIIB metals (i.e., Mn, Tc and Re). The present catalyst may comprise one or more catalytic forms of one or more noble metals (i.e., Pt, Pd, Ir, Rh, Os or Ru). Combinations of catalytic forms of such noble or non-noble metals, such as combinations of Pt with Sn, may be used. The valence state of the metal of the hydrogenation/dehydrogenation component is preferably in a reduced valance state, e.g., when this component is in the form of an oxide or hydroxide. The reduced valence state of this metal may be attained, in situ, during the course of a reaction, when a reducing agent, such as hydrogen, is included in the feed to the reaction.

Other elements, such as alkali (Group IA) or alkaline earth (Group IIA) compounds may optionally be added to or co-precipitated with the present catalyst to alter catalytic properties.

The Group IVB metal (i.e., Ti, Zr or Hf) and the Group VIB metal (i.e., Cr, Mo or W) species of the present catalyst are not limited to any particular valence state for these species. These species may be present in this catalyst in any possible positive oxidation value for these species. Subjecting the catalyst, e.g., when the catalyst comprises tungsten, to reducing conditions, e.g., believed to be sufficient to reduce the valence state of the tungsten, may enhance the overall catalytic ability of the catalyst to catalyze certain reactions, e.g., the isomerization of n-hexane.

The modified acidic oxide may be contacted with hydrogen at elevated temperatures. These elevated temperatures may be 100° C. or greater, e.g., 250° C. or greater, e.g., about 300° C. The duration of this contact may be as short as one hour or even 0.1 hour. However, extended contact may also be used. This extended contact may take place for a period of 6 hours or greater, e.g., about 18 hours. When zirconia is modified with tungstate and then contacted with hydrogen at elevated temperatures, an increase in catalytic activity, e.g., for paraffin isomerization, has been observed. The modified acidic oxide may be contacted with hydrogen in the presence or absence of a hydrocarbon cofeed. For example, the activity of the catalyst may be increased, in situ, during the course of a reaction, such as hydrocracking, when a hydrocarbon and hydrogen are passed over the catalyst at elevated temperatures.

The optional hydrogenation/dehydrogenation component of the present catalyst may be derived from Group VIII metals, such as platinum, iridium, osmium, palladium, rhodium, ruthenium, nickel, cobalt, iron and mixtures of two or more thereof. Optional components of the present catalyst, which may be used alone or mixed with the above-mentioned hydrogenation/dehydrogenation components, may be derived from Group IVA metals, preferably Sn, and/or components derived from Group VIIB metals, preferably rhenium and manganese. These components may be added to the catalyst by methods known in the art, such as ion exchange, impregnation or physical admixture. For example, salt solutions of these metals may be contacted with the remaining catalyst components under conditions sufficient to combine the respective components. The metal containing salt is preferably water soluble. Examples of such salts include chloroplatinic acid, tetraammineplatinum complexes, platinum chloride, tin sulfate and tin chloride. The optional components may also be co-precipitated along with the other components of the modified oxide material.

The present modified oxide material may be recovered by filtration from the liquid medium, followed by drying. Calcination of the resulting material may be carried out, preferably in an oxidizing atmosphere, at temperatures from about 500° C. to about 900° C., preferably from about 700° C. to about 850° C., and more preferably from about 750° C. to about 825° C. The calcination time may be up to 48 hours, preferably for about 0.1–24 hours, and more preferably for about 1.0–10 hours. In a most preferred embodiment, calcination is carried out at about 800° C. for about 1 to about 3 hours. The optional components of the catalyst (e.g., Group VIII metal, Group VIIB metal, etc.) may be added after or before the calcination step by techniques known in the art, such as impregnation, co-impregnation, co-precipitation, physical admixture, etc. The optional components, e.g., the hydrogenation/dehydrogenation component, may also be combined with the remaining catalyst components before or after these remaining components are combined with a binder or matrix material as described hereinafter.

In the present catalyst, of the Group IVB oxides, zirconium oxide is preferred; of the Group VIB anions, tungstate is preferred.

Qualitatively speaking, elemental analysis of the present acidic solid will reveal the presence of Group IVB metal, Group VIB metal and oxygen. The amount of oxygen measured in such an analysis will depend on a number of factors, such as the valence state of the Group IVB and Group VIB metals, the form of the optional hydrogenation/dehydrogenation component, moisture content, etc. Accordingly, in characterizing the composition of the present catalyst, it is best not to be restricted by any particular quantities of oxygen. In functional terms, the amount of Group VIB oxyanion in the present catalyst may be expressed as that amount which increases the acidity of the Group IVB oxide. This amount is referred to herein as an acidity increasing amount. Elemental analysis of the present catalyst may be used to determine the relative amounts of Group IVB metal and Group VIB metal in the catalyst. From these amounts, mole ratios in the form of $XO_2/YO_3$ may be calculated, where X is said Group IVB metal, assumed to be in the form $XO_2$, and Y is said Group VIB metal, assumed to be in the form of $YO_3$. It will be appreciated, however, that these forms of oxides, i.e., $XO_2$ and $YO_{31}$ may not actually exist, and are referred to herein simply for the purposes of calculating relative quantities of X and Y in the present catalyst. The present catalysts may have calculated mole ratios, expressed in the form of $XO_2/YO_3$, where X is at least one Group IVB metal (i.e., Ti, Zr, and Hf) and Y is at least one Group VIB metal (i.e., Cr, Mo, or W), of up to 1000, e.g., up to 300, e.g., from 2 to 100, e.g., from 4 to 30.

The amount of iron and/or manganese which is incorporated into the present acidic solid may also be expressed in terms of calculated mole ratios of oxides, based upon the elemental analysis of the solid for the Group IVB metal, X, along with Mn and Fe. More particularly, this acidic solid may have a calculated mole ratio, expressed in terms of $XO_2/(MnO_2+Fe_2O_3)$, of, for example, from 10 to 500. It will be appreciated, however, that Mn need not necessarily be in the form of $MnO_2$, and Fe need not be in the form of $Fe_2O_3$. More particularly, at least a portion of these components may be in the form of free metals or other combined forms than $MnO_2$ or $Fe_2O_3$ e.g., as salts with elements other than oxygen, in any possible valence state for X, Mn, or Fe. Accordingly, it will be understood that the expression, $XO_2/(MnO_2+Fe_2O_3)$, is given merely for the purposes of expressing calculated quantities of X, Mn, and Fe, and is not to be construed as being limited of the actual form of these elements in the present acidic solid material.

The amount of optional hydrogenation/dehydrogenation component may be that amount which imparts or increases the catalytic ability of the overall material to catalytically hydrogenate or dehydrogenate a hydrogenatable or dehydrogenatable organic compound under sufficient hydrogenation or dehydrogenation conditions. This amount is referred to herein as a catalytic amount. Quantitatively speaking, the present catalyst may comprise, for example, from about 0.001 to about 5 wt %, e.g., from about 0.1 to about 2 wt %, of the optional hydrogenation/dehydrogenation component, especially when this component is a noble metal.

Especially when the present catalyst includes a platinum hydrogenation/dehydrogenation component, this catalyst may also comprise up to about five weight percent of Fe and/or Mn, as measured by elemental analysis of the catalyst.

The present catalyst is acidic and may be observed as being highly acidic, even to the extent of being a superacid. Superacids are a known class of acidic materials which have an acidity greater than that of 100% $H_2SO_4$. This level of acidity may be determined by any appropriate means, including the use of suitable indicators, the determination of the ability to protonate certain chemicals, and/or the determination of the ability to stabilize certain cations, especially certain carbonium or carbenium ions. For example, this catalyst, whether analyzed in the presence or absence of optional components (e.g., hydrogenation/dehydrogenation components) and/or binder materials, may have an acid strength of a superacid as measured by the color change of an appropriate indicator, such as the Hammett indicator. More particularly, the Ho acid strength of the present catalyst may have a value of less than −13, i.e., an "acid strength" of greater than −13. The use of Hammett indicators to measure the acidity of solid superacids is discussed in the Soled et al. U.S. Pat. No. 5,157,199. This Soled et al. patent also describes the Ho acid strength for certain sulfated transition metal superacids.

The following examples illustrate the process of the present invention.

EXAMPLE 1

This Example describes the preparation of $Fe/WO_x/ZrO_2$. Five hundred grams of $ZrOCl_2 \cdot 8H_2O$ were dissolved with stirring in 6.5 liters of distilled $H_2O$. A solution containing 7.5 grams of $FeSO_4 \cdot 7H_2O$ dissolved in 500 ml of distilled $H_2O$ was then added to the zirconyl-containing solution. A third solution containing 263 mL of conc. $NH_4OH$, 500 mL of distilled $H_2O$, and 54 grams of $(NH_4)_6H_2W_{12}O_{40} \cdot x\ H_2O$ was added dropwise over a 30–45 minute period to the iron/zirconium mixture. The pH of the solution was adjusted to approximately 9 (if needed) by adding additional conc. $NH_4OH$ dropwise. This slurry was then placed in the steambox for 72 hours. The product formed was recovered by filtration, washed with excess $H_2O$, and dried overnight at 85° C. The material was then calcined in dry air to 825° C. for 3 hours.

EXAMPLE 2

The catalyst used in this example was prepared in accordance with Example 1 (8.53 g) was loaded into a stainless steel tubular reactor and bracketed by vycor chips which served as heat exchangers. After placing the reactor in a tube furnace, the catalyst was dried by heating for at least two hours to at least 300° F. in a stream of flowing nitrogen. The reactor temperature was adjusted to 375° F. at 600 psig, and filled with isopentane. A pre-mixed isopentane/pentene-1 feed stream (molar ratio=5.0) then was introduced at a flow rate of 0.08 gm pentenes/gm catalyst/hr. After passing pre-mixed feed through the reactor zone for 48 hrs. product was collected over the following 49 hrs. Product distributions were calculated from gc analyses of the gaseous and liquid products, and an additional simulated distillation ASTM 2887 of the liquid products. The total reactor effluent weight gave a 99.6% mass balance and showed the following distribution:

| Component | weight % |
| --- | --- |
| $C_3$-minus | 0.02 |
| Isobutane | 0.10 |
| n-Butane | 0.00 |
| Isopentane | 83.46 |
| n-Pentane | 0.40 |
| Cyclopentane | 0.00 |
| $C_6$-paraffin | 0.02 |
| Methylcyclopentane | 0.00 |
| $C_4$-olefin | 0.02 |
| Butadiene | 0.00 |
| $C_5$-olefin | 5.60 |
| Cyclopentene | 0.00 |
| $C_6$-olefin | 0.11 |
| Methylcyclopentane and Benzene | 0.00 |
| $C_7$-plus | 10.27 |
| Total | 100.00 |

Conversion of total pentenes was 65.8%. Calculated yields of isobutane and $C_6$-plus components per $C_5$-olefins converted (wt/wt) were:

| Fraction | Yields |
| --- | --- |
| $iC_4$ | 0.01 |
| $C_6$-300° F. | 0.07 |
| 300–400° F. | 0.61 |
| 400–650° F. | 0.28 |
| above 650° F. | 0.01 |
| Total | 0.98 |

About 25 g of squalane was added to a portion of the liquid product (20.4 g) to serve as a high boiling "chaser" during fractional microdistillation. After distilling the sample to a 300° F. endpoint at ambient atmospheric pressure, the residua were fractionated under vacuum (about 55 torr) to obtain a cut (10.4 g) with the intended kerojet boiling range from 300° F. to 400° F. The actual boiling range for this cut was estimated by simulated distillation analysis ASTM 2887. The boiling range and product properties for this sample were:

| Intended cut 300–400° F. | |
| --- | --- |
| Boiling Range (°F.) | |
| IBP | 208 |
| T10 | 311 |
| T50 | 335 |
| T90 | 351 |
| EP | 4030 |
| API gravity | 55.7 |
| Cetane Index | 51 |
| Cetane Number ($H^1$ nmr) | 15 |

After cooling, the residua were again distilled under vacuum (about 1–2 torr) to obtain a cut (4.94 g) with the intended diesel fuel boiling range from 400° F. to 650° F. The actual boiling range for this cut was estimated by simulated distillation analysis ASTM 2887. The boiling range and product properties for this sample were:

| Intended cut 400–650° F. | |
| --- | --- |
| Boiling Range (°F.) | |
| IBP | 309 |
| T10 | 434 |
| T50 | 478 |
| T90 | 564 |
| EP | 634 |
| API gravity | 44.5 |
| Cetane Index | 60 |
| Cetane Number ($H^1$ nmr) | 23 |
| wt. % Aromatics | 2.9 |

Changes and modifications in the specifically described embodiments can be carried out without departing from the scope of the invention which is intended to be limited only by the scope of the appended claims.

What is claimed is:

1. A process for converting a feedstock comprising at least one olefin and at least one isoparaffin to a product comprising distillate which comprises contacting said feedstock under conversion conditions with a catalyst composition which comprises an acidic solid comprising iron or manganese and a Group IVB metal oxide modified with an oxyanion of a Group VIB metal.

2. The process of claim 1, wherein said distillate contains less than about 35 wt. % aromatics.

3. The process of claim 1, wherein said distillate contains less than about 10 wt. % aromatics.

4. The process of claim 1, wherein said distillate has a cetane index of at least about 35.

5. The process of claim 1, wherein said distillate has a cetane index of at least about 45.

6. The process of claim 1, wherein the product boiling at a cut point up to about 450° F. is recycled to the contacting step.

7. The process of claim 1, wherein the product boiling at a cut point up to about 390° F. is recycled to the contacting step.

8. The process of claim 1, wherein said product further comprises gasoline.

9. The process of claim 1, wherein said conversion conditions include a temperature in the range of from about 100°–500° F.; a pressure in the range of from about 0 to about 1500 psig; an olefin WHSV (on catalyst basis) in the range of from about 0.01 to 10; and an isoparaffin:olefin molar ratio in the feedstock in the range of from about 0.1–100.

10. The process of claim 1, wherein said conversion conditions include a temperature in the range of from about 200°–400° F.; a pressure in the range of from about 50 to about 100 psig; an olefin WHSV (on catalyst basis) in the range of from about 0.1 to 5; and an isoparaffin:olefin molar ratio in the feedstock in the range of from about 0.25–50.

11. The process of claim 1, wherein said at least one olefin is selected from the group consisting of $C_2$–$C_{10}$ olefins.

12. The process of claim 11, wherein said at least one olefin is selected from the group consisting of $C_3$–$C_8$ olefins.

13. The process of claim 12, wherein said at least one isoparaffin is selected from the group consisting of $C_4$–$C_8$ isoparaffins.

14. The process of claim 1, wherein said at least one isoparaffin is selected from the group consisting of $C_4$–$C_5$ isoparaffins.

15. The process of claim 1, wherein said catalyst composition comprises iron.

16. A process for converting a feedstock comprising at least one olefin and at least one isoparaffin to a product comprising gasoline which comprises contacting said feedstock under conversion conditions with a catalyst composition which comprises an acidic solid comprising iron or manganese and a Group IVB metal oxide modified with an oxyanion of a Group VIB metal.

* * * * *